US008392215B2

(12) United States Patent
Tawil

(10) Patent No.: US 8,392,215 B2
(45) Date of Patent: Mar. 5, 2013

(54) METHOD FOR MEASURING HEALTH CARE QUALITY

(76) Inventor: Jack Joseph Tawil, Merritt Island, FL (US)

( * ) Notice: Subject to any disclaimer, the term of this patent is extended or adjusted under 35 U.S.C. 154(b) by 0 days.

(21) Appl. No.: 13/426,937

(22) Filed: Mar. 22, 2012

(65) Prior Publication Data

US 2012/0179487 A1 Jul. 12, 2012

Related U.S. Application Data

(62) Division of application No. 11/738,099, filed on Apr. 20, 2007, now Pat. No. 8,165,894.

(51) Int. Cl.
*G06Q 10/00* (2006.01)
*G06Q 50/00* (2012.01)
(52) U.S. Cl. ................................. 705/2; 705/3
(58) Field of Classification Search .................. 705/2–3
See application file for complete search history.

(56) References Cited

U.S. PATENT DOCUMENTS

| 5,018,067 | A | 5/1991 | Mohlenbrock et al. |
| 5,225,976 | A | 7/1993 | Tawil |
| 5,519,607 | A | 5/1996 | Tawil |
| 6,151,581 | A | 11/2000 | Kraftson et al. |
| 7,344,496 | B2 * | 3/2008 | Iliff .............................. 600/300 |
| 2004/0242972 | A1 * | 12/2004 | Adak et al. ................. 600/300 |
| 2006/0161456 | A1 * | 7/2006 | Baker et al. ....................... 705/2 |

FOREIGN PATENT DOCUMENTS

EP 297780 A2 6/1981

OTHER PUBLICATIONS

Drummond, M.F., M.J. Sculpher, G.W. Torrance, B. O'Brien and G.L. Stoddart. Methods for the Economic Evaluation of Health Care Programmes, 3rd Edition, Chapter 6 (Oxford University Press 2005).
Szilagyi, Peter G. "Managed care for children: Effect on access to care and utilization of health services." Children and Managed Health Care, 1998, vol. 8 (2). pp. 39-59.
Gold, Marthe R., Louise B. Russell, Joanna E. Siegel, Milton C. Weinstein. Cost-Effectiveness in Health and Medicine, Oxford University Press, New York. 1996. pp. 84-103.
Drummond, M.F., M.J. Sculpher, G.W. Torrance, B. O'Brien and G.L. Stoddart. Methods for the Economic Evaluation of Health Care Programmes, 3rd Edition, Chapter 6 (Oxford University Press 2005). Chapter 6.

* cited by examiner

*Primary Examiner* — Sheetal R Rangrej

(57) ABSTRACT

A method is presented for measuring the recovery of a medical treatment provider's patients from a given medical condition. During treatment and recovery, a patient periodically takes a survey to report the current intensity of the signs and symptoms caused by his/her medical condition. The patient also assigns a weight to each sign/symptom, indicating the relative intensity of his/her desire to eliminate it. The product of the intensity of a sign or symptom and its corresponding weight measures the diminishment of quality of life. An outcomes measure, measurable in quality-adjusted life-years, compares a patient's predicted recovery, which is rendered by an independent source at the time the patient's diagnosis is determined, with the patient's actual recovery. Outcomes measures for a provider's patients with a given medical condition and with similar predicted recoveries are combined to produce an unbiased, risk-adjusted outcomes index that can be compared with that of other providers.

20 Claims, 6 Drawing Sheets

METHOD FOR MEASURING HEALTH CARE QUALITY

CROSS-REFERENCE TO RELATED APPLICATIONS

This is a division of application Ser. No. 11/738,099, filed Apr. 20, 2007, now U.S. Pat. No. 8,165,894, granted Apr. 24, 2012, which is incorporated herein by reference.

FEDERALLY SPONSORED RESEARCH

Not Applicable

SEQUENCE LISTING OR PROGRAM

Not Applicable

BACKGROUND OF THE INVENTION

The ability to measure accurately health care quality—especially patient outcomes—has been elusive. While comparisons have been made of the health care quality of entire facilities (e.g., hospitals, health plans), little progress has been made with respect to providing unbiased and risk-adjusted performance measures for individual providers.

While some quality measurement systems, such as HEDIS [www.ncqa.org/programs/hedis/], compare compliance (e.g., the percentage of a provider's patients receiving vaccinations), none has been totally successful in providing a method for comparing the outcomes of individual providers. A persistent problem has been the difficulty in making comparisons of provider outcomes when patients initially face dissimilar recovery risks, due to illness severity, co-morbidities and other risk factors. Accordingly, methods and systems for making valid comparisons of provider outcomes are needed.

BACKGROUND OF THE INVENTION

1. Field of Invention

This invention relates to measuring the quality of health care delivered, and, more specifically, measuring patient outcomes with respect to changes in a patient's quality of life as a result of an episode of illness or injury and its treatment.

2. Prior Art

The prior art of record identified by the examiner of the parent application is cited below. The examiner's text directly relevant to the current divisional application is presented in italics.

The most remarkable prior arts of record are as follows:
Kraftson et al. —U.S. Pat. No. 6,151,581
Mohlenbrock et al. —U.S. Pat. No. 5,018,067
Baker et al. —U.S. Publication No. 2006/0161456
Adak et al. —U.S. Publication No. 2004/0242972e Kraftson teaches data for surveys administered to patients to provide quality of care, but fails to teach of providing a database of physicians and patients along with the physician's charge for a medical procedure, the outcomes index, prognosis rating of that procedure, historical data with patient outcomes ratings, and recovery score in quality-adjusted life-years; and furthermore creating a treatment plan and comparing the treatment plan to the actual treatment provided to the patient and comparing the recovery score and adjusting the recovery score within the database and then finally comparing the new outcomes index to other providers.

Mohlenbrock teaches claims processing to find benefits for patient, but fails to teach of providing a database of physicians and patients along with the physician's charge for a medical procedure, the outcomes index, prognosis rating of that procedure, historical data with patient outcomes ratings, and recovery score in quality-adjusted life-years; and furthermore creating a treatment plan and comparing the treatment plan to the actual treatment provided to the patient and comparing the recovery score and adjusting the recovery score within the database and then finally comparing the new outcomes index to other providers.

Baker teaches eligibility of patients with an insurance plan, but fails to teach of providing a database of physicians and patients along with the physician's charge for a medical procedure, the outcomes index, prognosis rating of that procedure, historical data with patient outcomes ratings, and recovery score in quality-adjusted life-years; and furthermore creating a treatment plan and comparing the treatment plan to the actual treatment provided to the patient and comparing the recovery score and adjusting the recovery score within the database and then finally comparing the new outcomes index to other providers.

Adak teaches recovery scores for treatments plans, but fails to teach of providing a database of physicians and patients along with the physician's charge for a medical procedure, the outcomes index, prognosis rating of that procedure, historical data with patient outcomes ratings, and recovery score in quality-adjusted life-years; and furthermore creating a treatment plan and comparing the treatment plan to the actual treatment provided to the patient and comparing the recovery score and adjusting the recovery score within the database and then finally comparing the new outcomes index to other providers.

Doyle teaches a claims processing system but fails to teach of providing a database of physicians and patients along with the physician's charge for a medical procedure, the outcomes index, prognosis rating of that procedure, historical data with patient outcomes ratings, and recovery score in quality-adjusted life-years; and furthermore creating a treatment plan and comparing the treatment plan to the actual treatment provided to the patient and comparing the recovery score and adjusting the recovery score within the database and then finally comparing the new outcomes index to other providers.

Szilagyi teaches utilization reports of health care services used for treatment, but fails to teach of providing a database of physicians and patients along with the physician's charge for a medical procedure, the outcomes index, prognosis rating of that procedure, historical data with patient outcomes ratings, and recovery score in quality-adjusted life-years; and furthermore creating a treatment plan and comparing the treatment plan to the actual treatment provided to the patient and comparing the recovery score and adjusting the recovery score within the database and then finally comparing the new outcomes index to other providers.

From the above prior art, only Adak and Baker are relevant to the current divisional application. The following patent application is also relevant. G. Brown et al. [U.S. Publication No. 2004/0111278] teaches a computer-implemented method and system for numerically quantifying an individual's loss of quality of life as the result of an accident causing an injury. The approach, based on health-utility analysis, is applied to provide an estimate of the amount of monetary damages in a tort case. The individual's health state prior to the injury, intermediate health states, and remaining life expectancy are associated with health-utility values of the same or similar health states. These latter are contained in a database of health-state utility values based on interviews of persons actually experiencing these health states. The health-state utility values are each weighted by the length of time the patient spends or is expected to spend in the corresponding health state and then summed up. This value is then compared with the health-state utility value of the patient's pre-accident state multiplied by that person's pre-accident remaining life expectancy. Brown fails to teach creating a set of reference recovery functions (RRFs), which are more consistent with a recovery that occurs as a smooth progression rather than as a series of discrete health states; generating a predicted recovery score by combining the prognosis rating with the RRFs; producing an actual recovery score solely from periodic surveys of the status of the patient's signs and symptoms, and including the patient's longevity; weighting each sign or symptom of the patient with respect to the intensity with which the patient wishes to eliminate the sign or symptom; generating a personal recovery function by interpolating the patient's recovery path with respect to the RRFs; calculating a recovery score as the area beneath the patient's recovery path; calculating an outcomes measure by combining the patient's predicted recovery score with the actual recovery score; and showing how to modify the outcomes measure with respect to the patient's actual life span once the patient expires.

Another relevant patent application is M. Brown et al. [U.S. Publication No. 2007/0179809], which teaches a system and method for performing a cost-utility analysis with respect to pharmaceutical interventions. The focus of this invention is on comparing a plurality of alternative pharmaceutical interventions to determine the optimal intervention, whereas the focus of the current invention is on how well an individual patient recovers following treatment from a medical provider. As with G. Brown, M. Brown fails to teach creating a set of reference recovery functions (RRFs); generating a predicted recovery score by combining the prognosis rating with the RRFs; producing an actual recovery score solely from periodic surveys of the status of the patient's signs and symptoms, and including the patient's longevity; weighting each sign or symptom of the patient with respect to the intensity with which the patient wishes to eliminate the sign or symptom; generating a personal recovery function by interpolating the patient's recovery path with respect to the RRFs; calculating a recovery score as the area beneath the patient's recovery path; calculating an outcomes measure by combining the patient's predicted recovery score with the actual recovery score; and showing how to modify the outcomes measure with respect to the patient's actual life span once the patient expires.

U.S. Pat. No. 5,519,607 (1973), issued to the current inventor, is also a relevant prior art record. This patent teaches an independently produced prognosis rating and a recovery rating, preferably generated by a panel of experts, and comparing the prognosis rating with the recovery rating. However, this patent fails to teach creating a set of reference recovery functions (RRFs); generating a predicted recovery score by combining the prognosis rating with the RRFs; producing an actual recovery score solely from periodic surveys of the status of the patient's signs and symptoms, and including the patient's longevity; weighting each sign or symptom of the patient with respect to the intensity with which the patient wishes to eliminate the sign or symptom; generating a personal recovery function by interpolating the patient's recovery path with respect to the RRFs; calculating a recovery score as the area beneath the patient's recovery path; and calculating an outcomes measure by combining the patient's predicted recovery score with the actual recovery score.

In the published literature, the following volume is also relevant, especially Chapter 6 dealing with Cost-Utility Analysis. *Methods for the Economic Evaluation of Health Care Programmes,* 3rd Edition by M. F. Drummond, Mark J. Sculpher, G. W. Torrance, B. O'Brien and G. L. Stoddart (Oxford University Press 2005). The Health Utilities Index (HUI) and its variations are presented in this book along with various other methods for evaluating health care programs. The HUI is used primarily to assess the comparative effectiveness of a treatment with respect to alternative treatment methods, whereas the outcomes index developed herein is used to rate medical providers. In the former approach, an outcomes measure is estimated for each medical condition, and a value between 0.0 and 1.0 is assigned to represent the quantity of Quality-Adjusted Life-Years (QALYs) that are lost by an individual who has that medical condition. This source does not teach the methodology that is used to derive each outcomes measure. More importantly, the outcomes measures are not developed for individual risk categories (prognosis-rating groups), as taught by the current invention. The HUI is also based on a fixed survey instrument that is administered to all individuals with the given medical condition. The outcomes measure for the current invention, on the other hand, relies on the specific signs and symptoms experienced by the particular patient, each weighted by the patient's desire to eliminate it, as well as her total loss of QALYs. Although the outcomes index can measure loss of utility in terms of QALYs, it is not used to make interpersonal comparisons among patients, as is the case, if only implicitly, with the HUI. Drummond et al. cites the preference-based health measure from the EuroQol Group [see "Health Policy under EuroQol: A New Facility for the Measurement of Health-Related Quality of Life by the EuroQol Group" (1990).] It, too, uses a fixed survey instrument to assess the quality of life of an individual with a medical condition and differs from the current invention in the same ways that the HUI differs.

OBJECTS AND ADVANTAGES

Accordingly, the objects and advantages of this method for measuring health care quality include the following:

for a given medical episode, the issuance of a prognosis rating prior to the beginning of treatment by a diagnostic physician or other source independent of the treating physician facilitates producing a measure of the patient's recovery that is unbiased;

the assessment of the patient's recovery is from the patient's own perspective, which is the foundation for an ideal measure of an individual's well-being or quality of life;

a formula based on a plurality of individual patient assessments can provide an objective measure that quantifies patients' assessment of their recovery progress/regress;

grouping patients according to their prognosis ratings enables risk-adjusted comparisons of doctors' recovery rates, as patients within a given prognosis rating group face or faced comparable recovery risks;

the outcomes measure is based exclusively on changes in the quality and quantity of life, which make it amenable to being measured in quality-adjusted life-years (QALYs);

outcomes measures are readily compiled into an unbiased and risk-adjusted outcomes index that can be used to compare how well patients within a given prognosis rating group and with a given medical condition recover when treated by individual physicians;

the methodology, when used in conjunction with the parent invention, is structured such that by achieving the best outcome for himself/herself, the treatment provider also provides the best recovery value for his/her patient;

use of the outcomes index does not require making interpersonal comparisons;

a "value" chart can be produced showing the relationship between treatment cost and outcomes index, as shown in FIG. 6;

the outcomes index can be used to evaluate and compare the outcomes history of different treating physicians with respect to a given medical condition and a given prognosis-rating group;

the outcomes index can produce unbiased and risk-adjusted outcomes measures using a fully automated process;

the outcomes index can be used to evaluate and compare the outcomes history of different hospitals and other care facilities;

the outcomes index can be used by care providers to rate their own performance and to identify potential areas of improvement;

the outcomes index can be used to evaluate a treating doctor and to identify potential areas of improvement;

the outcomes index can be used by a patient for selecting a treatment plan or a treatment provider;

the outcomes index can be used by insurers for ratings of care providers such as treating doctors the outcomes index can be used by an insured for selecting an insurer; and the outcomes index can be used generally as a decision support document.

SUMMARY OF THE INVENTION

In this specification, a distinction is made between an episode of illness or injury and the type of illness or injury. The former refers to a single instance of an illness or injury, while the latter refers to a category of illness or injury. For example, the latter could comprise the ICD-9-CM (International Statistical Classification of Diseases and Related Health Problems) codes commonly in use in the medical profession.

It is an object of the present invention to provide an unbiased and risk-adjusted method for quantitatively evaluating patient outcomes that will facilitate comparisons of providers on a diagnostic-specific basis. It is a further object to make this method automated, when used in conjunction with the parent invention.

One aspect of the present invention provides a method for combining data from patients and physicians; another aspect provides a method for quantifying how quickly and completely a provider's patients recover. The latter method provides for the comparison of patient outcomes of different providers treating the same medical condition.

The method for measuring health care quality comprises creating a set of reference recovery functions (RRFs) for one or more medical conditions, generating a predicted recovery score for a patient for a given medical episode, administering a plurality of surveys with respect to the signs and symptoms of the patient, calculating a survey score from each survey, generating a personal recovery function from all of the survey scores for the medical episode, calculating an actual recovery score from the personal recovery function, and calculating an outcomes measure that combines the predicted recovery score with the actual recovery score. The outcomes index is a compilation of the outcomes measures for a plurality of patients of a given provider within a single prognosis-rating group, all with a given medical condition.

Methods are also disclosed for incorporating co-morbidities and mortalities into the assessment of a patient's recovery.

All of the functions of the present invention can be automated. These include patient-administered surveys for assessing provider quality and a method for measuring and comparing risk-adjusted patient outcomes. The invention includes a database that can track health care quality data; a first processor that can administer any patient surveys that are scheduled, process quality indicators derived from the surveys, and distribute to insureds quality information on those providers who can provide the treatments needed by the insured; a second processor that can administer any patient surveys that are scheduled; and a third processor that can maintain patient outcomes measures and other measures of health care quality, as well as to obtain death notices from vendors such as the Social Security Administration's Death Master Updates.

DETAILED DESCRIPTION OF THE INVENTION

The following is a list of terms utilized throughout this specification:

Administrator: The entity that performs the tasks typically performed by the administrator of a health care plan, including but not limited to enrollment, eligibility confirmation, claims preparation, processing and adjudication, patient billing, account maintenance, database maintenance, and fraud detection.

Insurer: The entity that provides health insurance or a prepaid health plan to a number of parties.

Insured: A party that is insured by the insurer, including the person and his or her dependents covered by a policy issued by the insurer.

Outcomes Index, or, equivalently, outcomes rating: A numerical index derived from the recovery scores of a number of patients with the same diagnosis and with prognosis ratings within a given range.

Outcomes Measure: The numerical value resulting from combining the recovery scores of a patient, and that may include his/her predicted recovery score or prognosis rating.

Patient: A person receiving health services.

Personal Recovery Function: A patient's interpolated recovery path that goes through each survey score.

Provider: Any person or entity providing medical or health-related services.

Physician: A doctor who conducts an initial or diagnostic examination of an insured to determine the patient's diagnosis and what medical services are needed.

Prognosis Rating: A predicted numerical value of a patient's recovery from a specific illness or injury.

Recovery Score: The numerical value of a patient's recovery, based on two or more survey scores.

Reference Recovery Function: The statistically estimated curve that is fitted to a number of survey scores or survey score sets.

Survey: A set of statements or questions designed to quantify a patient's current health care status with respect to a specific illness or injury;

Survey Score: The numerical value of a completed survey.

Survey Score Set: One or more survey scores pertaining to an episode of illness or injury of a single patient.

Figure 1:
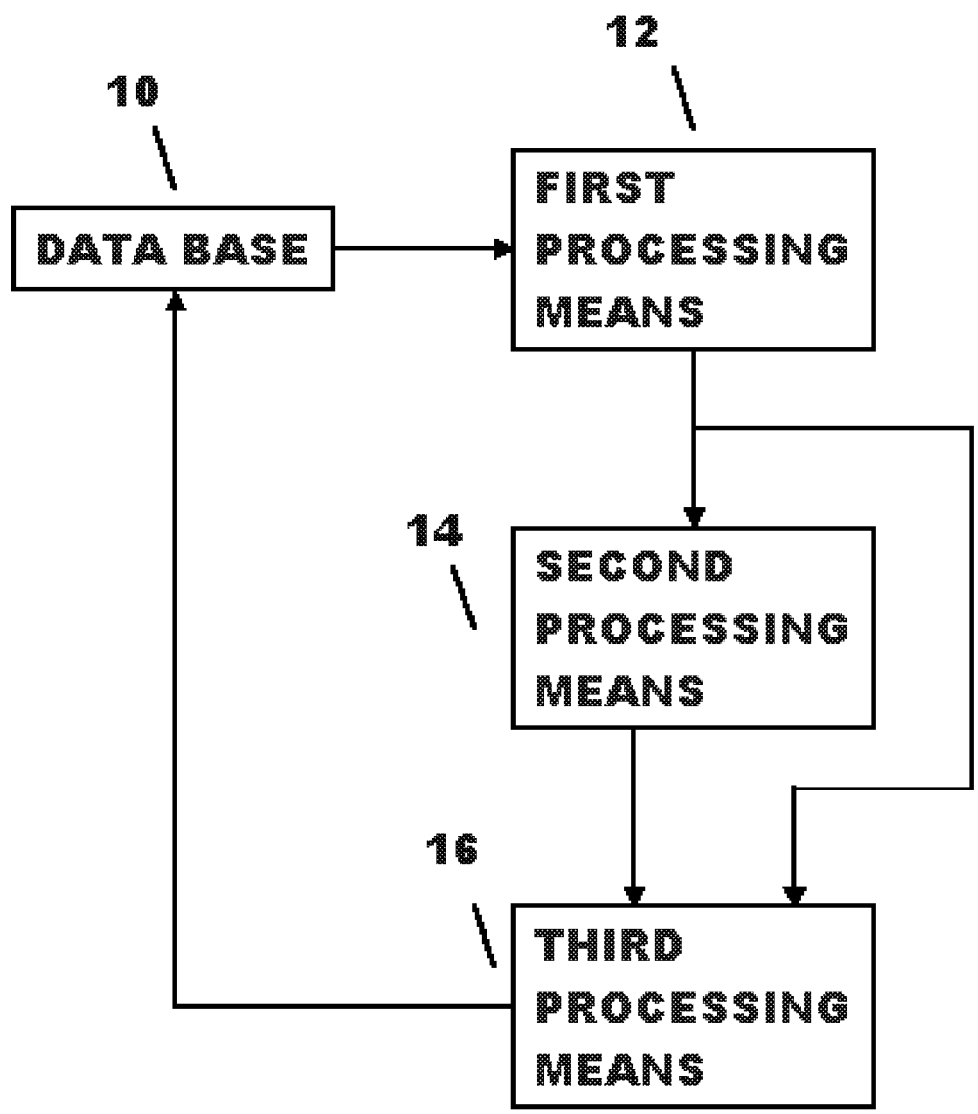
FIG. 1 illustrates a block diagram showing the relationships between the database and the three processing means.

U.S. Pat. No. 5,225,976 taught that the diagnostic function would be separate and distinct from the therapeutic function and that the diagnosing physician would be either under contract to or an employee of the health plan, and therefore that his/her fealty would be with the health plan. Referring to FIG. 1, the health care delivery system taught by U.S. Pat. No. 5,225,976 can be implemented in a variety of ways. The first processing means 12 is provided in the offices of each physician performing diagnostic examinations, and the second processing means 14 is provided in the offices of each provider performing medical treatment procedures. The interconnections between the database 10 and each processing means in each office are provided as illustrated in FIG. 1 via some communications network. The database 10 is preferably provided in each first processing means 12, but can also be provided in the third processing means 16 for access by each first processing means 12. In an alternative embodiment, the database 10, the first processing means 12, the second processing means 14 and the third processing means 16 can be part of a central processor. In this case, data entry means are provided in the office of each physician who performs diagnostic examinations to provide access to the first processing means 12 in the central processor. Also, data entry means are provided in the office of each provider who performs medical procedures to permit access to the second processing means 14.

The database 10 contains each patient's medical history record and other medical information that may be useful in determining a patient's prognosis rating. For example, it may include an emergency record that typically consists of the name of the family doctor, whom to notify in case of an emergency, drug allergies, serious illnesses, device (e.g. a pacemaker) or organ implants, other medical information and religious preference.

The information in the database 10 can be stored on any type of storage media, for example, on floppy disk, flash drive or any other type of magnetic media. It can also be stored on a central processor and it is preferred that the third processor 16 maintain a copy of this portion of the database 10.

U.S. Pat. No. 5,519,607 teaches how this system can incorporate a rating system that measures the quality of care provided to the insured. When a diagnostic physician is preparing the treatment plan utilizing the first processing means 12, the insured is assigned a prognosis rating, which indicates the expected recovery response of the insured following a treatment program by a medical treatment provider of average ability. The prognosis rating is preferably a number on an arbitrary scale, say from zero to ten. A prognosis rating of ten would indicate the most optimistic prognosis, while progressively lower numbers would indicate that a less optimistic recovery is expected. The prognosis rating depends on the severity of the patient's illness, as well as on other relevant risk factors, such as age, heavy smoking and co-morbidities. The prognosis rating can then be reported from the diagnostic physician to the patient in a separate document. Additionally, the prognosis rating is transmitted by the first processing means 12 to the third processing means 16.

The third processing means 16 then adds this information to the database 10. For each medical treatment provider, the database 10 will include information, i.e., an outcomes score or index, indicating how well insured patients having a given type of illness or injury and a given prognosis rating responded to the treatment; then, the actual outcome is compared with the expected outcome via some scoring method, which is a subject of the current patent application. As described earlier, the resulting information is then available for each insured patient to decide which medical treatment provider to select. For example, this information can then be presented to the insured in a graphical format showing, for each medical treatment provider, the prognosis rating on the vertical axis and the outcomes score on the horizontal axis.

Figure 2:
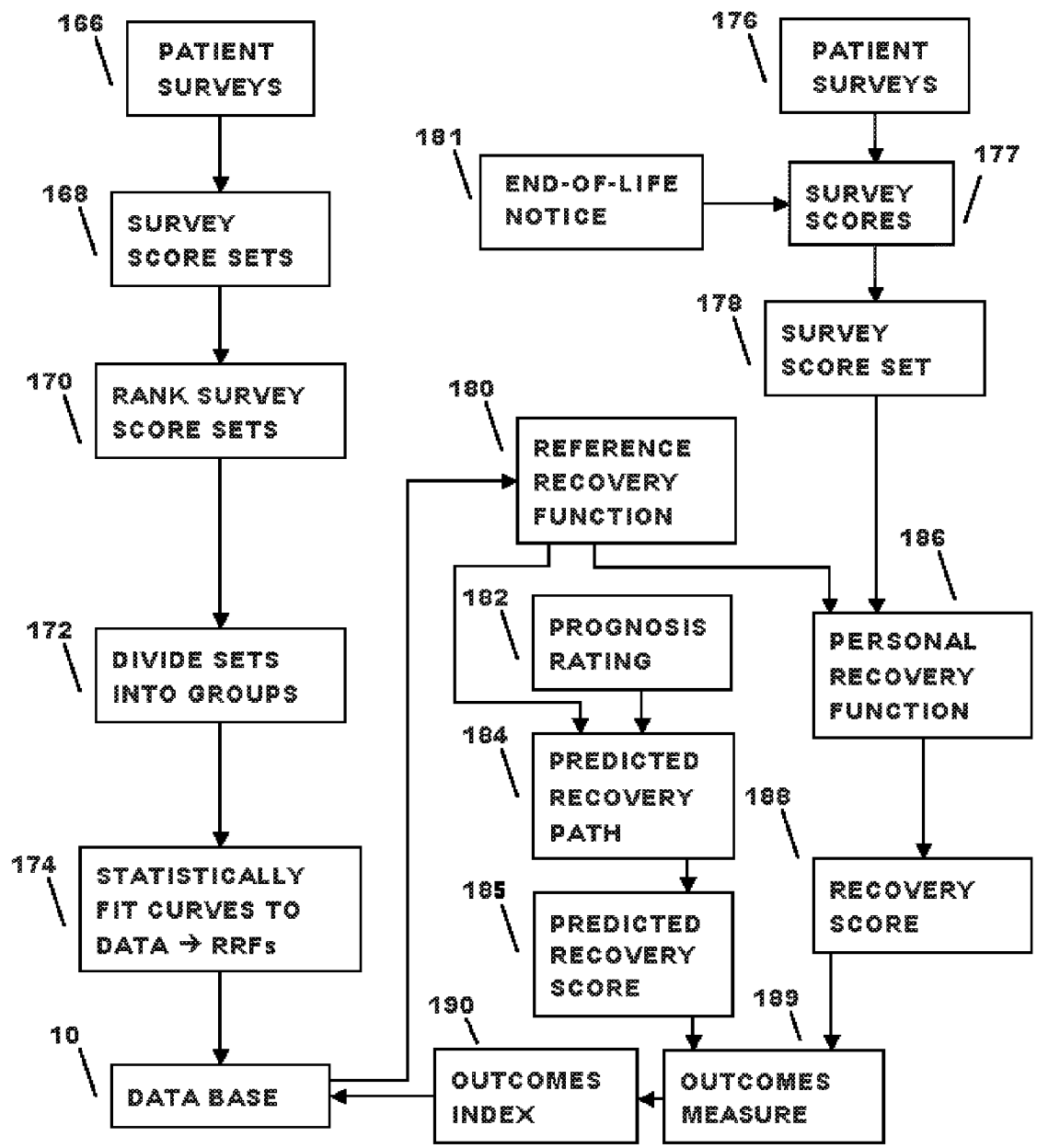
FIG. 2 illustrates a block diagram of a method for quantifying patient outcomes in accordance with a preferred embodiment of the present invention.

As an aspect of the present invention, a method is disclosed for comparing a patient's actual recovery score 188 with the patient's predicted recovery score 185, as shown in FIG. 2. This figure shows that initially a number of surveys 166 is utilized to produce a set of reference recovery functions 180, as explained below. These RRFs are then applied to subsequent surveys to obtain a recovery score 188. The foundation of this methodology is a set of surveys 176 that seeks to quantify the progress over time of a patient's health status, preferably as viewed from the patient's own perspective.

When the insured visits a physician or medical treatment provider, a survey 176 is completed. In the preferred embodiment, the survey is self-administered using a data entry device, and, if the patient is being examined by a diagnostic physician, the survey may be presented to the patient by the first processing means 12; if the patient is being treated by a medical treatment provider, it may be presented by the second processing means 14; or, alternatively, it may be presented by some other processing means that may or may not be sited in a provider's office. For example, the input device could be the patient's home computer.

The survey 176 preferably requires that the patient report all signs and symptoms experienced during some recent period and which fall into any of, say, three categories: physical, sensory and functional. These quality-of-life changes in health status are called illness/injury-related effects, or IREs. Physical IREs relate to such factors as scars, acne, amputations and other types of disfigurement. Sensory IREs relate to such sensations as pain, itching, ringing in ears and other symptoms that affect the senses. Finally, functional IREs refer to impairments in the ability of a person to function or perform specific activities with the same proficiency as immediately prior to the onset of the illness or injury. In an alternative embodiment, mental effects, such as apprehension and anxiety, can also be included in the survey.

The purpose of the survey 176 is to identify and characterize each IRE that is related to the illness or injury of the patient. In the preferred embodiment, the patient assigns to each IRE a value that depends on the patient's perception of its severity, say, on a scale of 0 to 10. Call this its severity score. After the survey is completed, in one embodiment, the diagnostic physician reviews the patient's survey and identifies all of the IREs that appear to be related to the patient's current diagnosis. It is this subgroup of IREs that is used to compute a survey score 177 for the patient. In the preferred embodiment, the database 10 already contains all of the IREs associated with each illness and injury. If the IRE is not in the database with respect to that type of illness or injury, then it is not scored with respect to the current illness or injury, although the diagnostic physician may override this decision. When a notice of death 181 is obtained, and the medical episode is a contributing factor to the patient's death, a final survey score is computed.

For the patient, the ideal outcome is one in which longevity is no less than prior to the onset of the episode of illness or injury, and all of the associated signs and symptoms are eliminated immediately. The patient is the best evaluator of these effects; death is an objective fact. Therefore, periodic input from a living patient is all that is required to mechanically compute a survey score from the patient's survey.

The preferred embodiment of the present invention measures the relative reduction or increase in the levels of the IREs over time, weighted by the "concern" that the patient has with each; i.e., it measures the patient's recovery progress, in terms of quality-of-life changes, as self-determined by the patient. In the preferred embodiment, the weights are obtained as follows: After all of the patient's IREs have been identified and characterized by severity, they are presented to the patient by means of a display device connected to a data entry device. The patient then assigns a weight to each IRE representing the intensity of the patient's desire to eliminate it. For example, the patient could be informed that she can spend a maximum of $100 to eliminate all of the listed IREs. Then she would be asked to indicate the most that she would be willing to spend from her $100 budget to eliminate each one.

It can be inferred that the greater the patient's willingness to spend on a particular IRE, the greater the desire to eliminate it. Based on these weights, a medical treatment provider can assess how best to alleviate the patient's IREs. Moreover, the provider will maximize his own outcomes score 189 by maximizing the patient's future survey scores 177.

At subsequent visits to a provider with electronic access to the third processing means 16, the patient inputs the current status of his/her IREs, re-scoring the severity of previously specified IREs and adding and scoring any new ones.

Referring again to FIG. 2, the patient's recovery score 188 is derived from all of the survey scores 177 for the current episode of illness or injury; together, these comprise a survey score set 178. Preferably, each IRE, $I_{it}$, is scored on a ten-point scale: the higher the score, the more intensely does the patient perceive the IRE. The patient's normalized survey score 177 for a survey taken at time t is $$S_t = 10.0 - \Sigma w_{it} I_{it} / \Sigma w_i,$$

where $w_i$ ($0 \leq w_i \leq 1$) is the weight that the patient has assigned to the i-th IRE, and I is its severity. In the preferred embodiment, the patient may supply new weights with each survey. In an alternative embodiment, the weights are assigned during the initial survey, but do not change over the course of the patient's recovery.

The normalized weighted sum, $(\Sigma w_{it} I_{it})/\Sigma w_{it}$, of the IRE scores lies between 0 and 10, with higher values associated with more severe signs and symptoms. Since higher prognosis ratings 182 are associated with less severe signs and symptoms, the weighted sum is subtracted from 10.0 to synchronize the survey scores with the prognosis ratings. The normalized weighted sum is also a quality-of-life measure. To convert each normalized weighted IRE score, $(w_{it} I_{it})/\Sigma w_{it}$, for the i-th IRE into QALYs, the score is multiplied by a constant, which is equal to the loss of QALYs attributable to the patient's medical condition at time t divided by the sum of the normalized IRE scores. Strictly speaking, the QALY changes experienced by the patient are the product of the conversion factor times each weight, or intensity factor. The intensity factors themselves also can be viewed as weights that modify the QALYs by the severity of the patients' IREs. Each RRF, then, embodies the average weighting of those IREs within its corresponding prognosis rating group.

The next step is to develop reference recovery functions (RRFs) 174 and 180; these are the benchmarks against which the patient survey scores are to be compared. In the preferred embodiment, nine RRFs are constructed, which will facilitate ten prognosis rating groups. The $RRF_p$ (p=1, . . . , 9) are statistically fitted curves showing the expected recovery path of an average patient with a prognosis rating between p and p+1. A set of nine RRFs is shown in FIG. 13. The ordinate axis is an index scale from 0 to 10—it is also the scale for survey scores after they have been converted into QALYs times ten. $RRF_{10}$ is the horizontal line at the top of the figure; it corresponds to "bliss", a complete absence of IREs. $RRF_0$, the horizontal line at the bottom of the figure, corresponds to death.

Each RRF 174 is derived from a large number of survey score sets 168, a set being defined as all of the survey scores for an individual with respect to a single episode of illness or injury. In the preferred embodiment, the survey score sets 168 first are divided into groups according to their prognosis ratings before ranking them 170 and then subdividing them 172. In an alternative embodiment, the arithmetic mean or other average statistic of each set of survey scores is first computed. These mean scores are preferably sorted in descending order 170 and then preferably divided into approximately nine groups 172. Each group 172 consists of a sufficiently large number of survey scores so as to provide statistical significance when the curves are statistically fitted to the data 174. In both embodiments, the following treatment is then applied to each subgroup.

In a preferred embodiment, a curve is statistically fitted to the individual survey scores in each group, using a technique such as least squares. In another embodiment, the curve is fitted to the means of the survey score sets 168 comprising each data group. The type of curve that provides the best statistical fit to the data will likely depend on the characteristics of the recovery function for a particular type of illness or injury. Possible curve types include polynomial functions, elliptical and other conic functions, transcendental functions, as well as linear, linear-logarithmic and mixed functions. All functional types are within the scope of the present invention. An improved fit may also be obtained by estimating with separate functions the different phases of a patient's recovery (e.g., the "initial" or "stabilization phase," the "maintenance phase" and the "terminal phase" of a chronic illness).

Once the RRFs are produced, they are added to the database 10 and become available at step 180 for scoring the predicted 184 and actual recovery path (personal recovery function) 186 and recovery score 188. Over time, it is preferred to update the RRFs by using more recent survey score sets 168 to reflect advances in medical techniques and technologies.

The best way to characterize each RRF graphically is by the area under its curve, where the abscissa is measured in years, and the ordinate axis measures the absence of IREs, i.e., the quality of life. This area, when divided by 10 (the upper value of the index), represents "quality-adjusted life-years (QALYs)," if the survey scores first have been converted to QALYs (see "Theoretical Foundations of Cost-Effectiveness Analysis," in Cost-Effectiveness in Health and Medicine, Gold, Marthe R. et al., 1996).

Once the RRFs have been estimated for a given type of illness, the individual's personal recovery function (RF) 186 is statistically fitted through a set of survey scores 178. The area under the RF, between the first and last survey score in the set, equals the patient's recovery score (RS) 188. Graphically, the personal RF 186 is a curve that goes through each survey score.

To construct the personal RF, first connect each pair of adjacent survey scores by a line segment. Then treat each line segment sequentially. The personal RF will be a curve that lies above, below or on the line segment and its curvature will be based on the curvatures of the RRFs immediately above and below the line segment.

Figure 3:
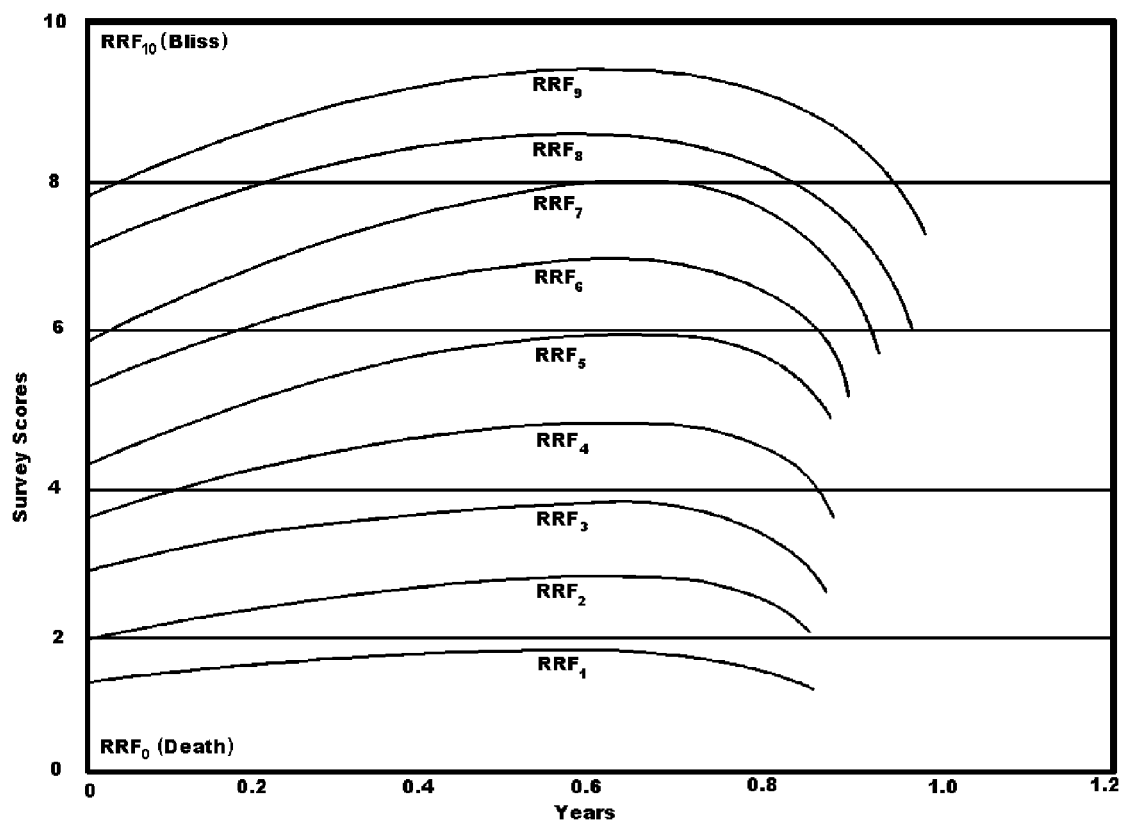
FIG. 3 illustrates a set of reference recovery functions for measuring patient outcomes.
Figure 4:
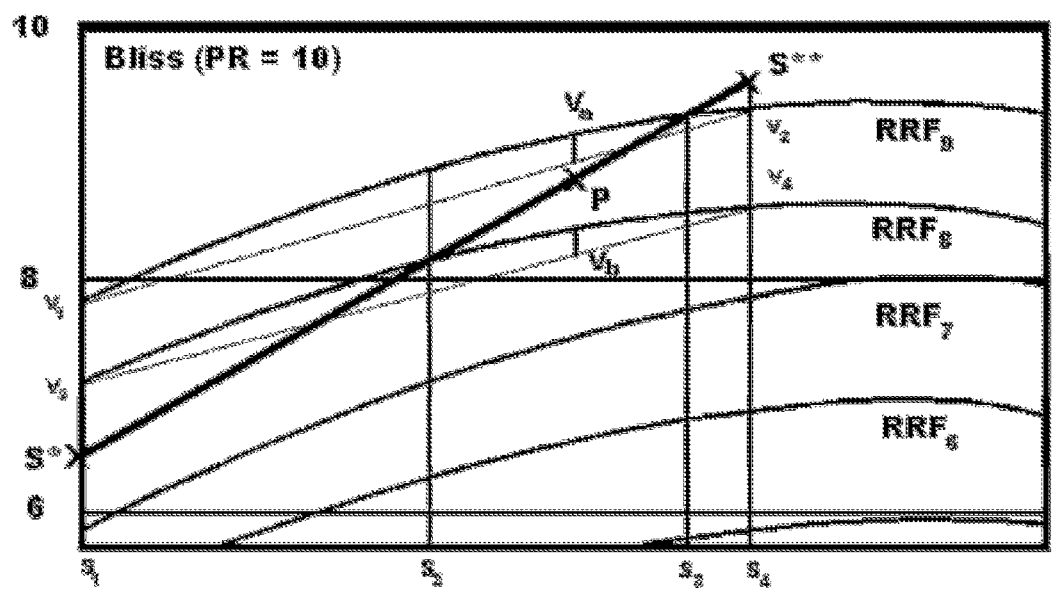
FIG. 4 illustrates a method for estimating a personal recovery function.

FIG. 4, which is an enlarged section of FIG. 3, shows how to construct a personal recovery function curve between two survey scores, S* and S**, respectively. This curve, which is not shown, will lie above the line segment S* S and will assume the curvature characteristics of the nearby RRFs. First, drop vertical lines from the two survey scores and from each intersection of the survey score line segment with an RRF. In FIG. 4**, the four vertical lines intersect the abscissa at $S_1$, $S_2$, $S_3$ and $S_4$. Next, construct a chord between the two points at which the vertical lines at $S_1$ and $S_4$ intersect each of the relevant RRFs. $V_1$ and $V_2$ are the endpoints of the chord for $RRF_9$, and $V_3$ and $V_4$ are the endpoints of the chord for $RRF_8$.

$V_a$ and $V_b$ are the vertical distances between the chords and their corresponding RRFs. Note that $V_a$, $V_b$ and P are aligned on the same vertical, where P is an arbitrary point along the line segment S* S. Determine a distance V that is vertically above P, and which is a weighted average of the distances $V_a$ and $V_b$. If P lies between, say, $RRF_8$ and $RRF_9$, then the weights will depend on the vertical distance of the point P from the corresponding chords for $RRF_8$ and $RRF_9$: the closer is P to the chord for $RRF_9$, the larger the weight assigned to $V_a$ relative to $V_b$; and, conversely, the closer P is to the chord for $RRF_8$, the larger the weight assigned to $V_b$ relative to $V_a$.

Similarly, construct a series of other vertical distances between $S_2$ and $S_3$. The locus of points connecting the tops of these distances is one portion of the curve that is constructed above S* S**. Another portion of the curve is constructed between $S_1$ and $S_2$ in the same way, but using the chords for $RRF_7$ and $RRF_8$. Finally, the portion of the arc between $S_3$ and $S_4$ is constructed using the chord for $RRF_9$ and $RRF_{10}$, the "bliss" line. The curves thus constructed between $S_1$ and $S_2$, $S_2$ and $S_3$, and $S_3$ and $S_4$ together comprise the personal RF.

To calculate the recovery score, RS 188, determine the area below the personal RF between $S_1$ and $S_4$, which is easily computed using Simpson's Rule (see any standard calculus text), and then divide by 10. As discussed earlier, in the preferred embodiment, this area is in units of QALYs. Call this area $RS_{idp}$, where the subscript refers to the i-th patient, d-th diagnosis, and p-th prognosis rating.

Next, compare the patient's recovery score 188 with the predicted recovery score 185 based on the patient's prognosis rating 182. As before, compute the area under a curve between $S_1$ and $S_4$ using Simpson's Rule, but this time for the RRF associated with the patient's prognosis rating. If the patient's prognosis rating 182 contains a fractional part, such as 7.2, then the predicted recovery score is interpolated from the RRFs that bracket the prognosis rating, i.e., $RRF_7$ and $RRF_8$. First, compute $A_7$ and $A_8$, the areas under $RRF_7$ and $RRF_8$, respectively. Then the predicted recovery score, PS, in QALYs is $$PS = (A_7 + (PR - int(PR))(A_8 - A_7))/10,$$

where int(PR) is the integer value of the prognosis rating. In the example, int(7.2)=7.

There are several ways to combine the recovery scores of patients to obtain an outcomes measure 189 for a provider. One measure is $$M_{dp}^* = (\Sigma_i (RS_{idp}/t_i))/I,$$

where $t_i$ is the total number of actual years over which the recovery score is measured for the i-th patient, and I is the total number of patients being scored. Note that the best possible score for M* is 1.0 and occurs only if a doctor has eliminated all of the IREs of all of the patients in this group instantly and completely and has fully restored their longevity. The closer is M* to 1.0, the closer is the doctor to perfection.

Another measure is $$M_{dp}^{+} = (\Sigma_i (RS_{idp}/PS_{idp}))/I.$$

This is the sum of the ratios of patients' actual recovery scores 188 to their predicted recovery scores 185, divided by the number of patients, I. A value of 1.0 indicates that the doctor, on average, just meets expectations, while a higher (lower) value indicates that he exceeds (falls short of) expectations.

A third measure is $M_{dp}^{\#} = \Sigma_i RS_{idp} / \Sigma_i PS_{idp}$.

A fourth embodiment is to estimate statistically the following relationship, using all doctors' patients, i, having a diagnosis d and prognosis rating in group p:

$$Y_{idp} = b_0 + b_1 M_{idp}^* + b_2 M_{idp}^{\#} + b_3 PR_{idp} + b_4 \ln Q_{idp} + u,$$

where $Y_{idp}$ is the actual outcome in QALYs, $M_{idp}^*$ and $M_{idp}^{\#}$ are as defined above, $PR_{idp}$ is the prognosis rating, $\ln Q_{idp}$ is the natural logarithm of the number of times the doctor has performed the treatment, $b_0, \ldots, b_4$ are parameters to be estimated, and u is a randomly distributed error term.

Once this relationship is estimated, then $Y_{idp}$ is computed for each doctor with respect to his i patients in the dp-th category, using the estimated parameter values. Finally, the arithmetic mean of the $Y_{idp}$ is computed for each doctor, which becomes that doctor's Outcomes Index.

An empirical analysis can be applied to determine which of the above or other measures of the Outcomes Index is preferred. The selection of the preferred measure would therefore be empirically determined and applied. The preferred measure can vary by illness or by other factors.

It is preferred that the Outcomes Index remains a dynamic measure, because improvements in outcomes will evolve with medical practice and technology. Therefore, it is preferred that the RRFs be re-estimated from time to time with more recent survey score sets.

This raises the question of whether previously computed RSs 188 and personal RFs 186 are to be recomputed each time the RRFs are updated. It is preferred, in order to maintain stability in the Outcomes Index, that survey scores not be re-computed using the latest RRFs. Thus, an Outcomes Index will likely be based on recovery scores that are themselves based on different vintages of the RRFs.

The Effect of Co-Morbidities

Co-morbidities present a special problem in that two or more diagnostic codes may be involved, and two or more providers may have lead responsibilities. The effects of each disease and the responsibilities for the patient's recovery must be disentangled.

Several embodiments to the co-morbidity problem are presented within the scope of the present invention. The simplest embodiment is not to address the co-morbidities explicitly. This means the RRFs 180, and therefore the Outcomes Index 190, may include multiple diagnoses. For example, the RRFs produced for Chagas heart disease (ICD-9 0860) might include the effects of the same patient's melanoma (as a co-morbidity). In this example, the Outcomes Index of the doctor treating the patient's melanoma could be affected by the performance of the doctor treating the Chagas heart disease, and vice versa. A further disadvantage is that this solution would likely increase the variance of the survey score sets 170 that comprise the RRFs 180, which would in turn make the Outcomes Index 190 a less-precise measure of a provider's performance.

A second embodiment excludes all cases involving significant co-morbidities. For example, if a patient has both colon cancer and diabetes, that patient's survey scores for these diseases are excluded entirely. A disadvantage with this approach is that doctors would know that they are not being evaluated for patients with serious co-morbidities and might be less conscientious as a result. For the provider whose treatment of a patient is not going well, there is also the perverse incentive to "find" some co-morbidity for the patient so that the patient's recovery score will not count in his Outcomes Index.

A better embodiment is to adjust the original prognosis rating 182 whenever the patient contracts a new illness, provided that the new illness is not a complication of an existing illness. In this case, the diagnostic physician assigns a prognosis rating 182 to the new illness, taking into consideration the likely effect of the original illness on the patient's recovery. A diagnostic physician also assigns a new prognosis rating to the original illness, given that the new illness will likely also affect the patient's recovery from the original illness. All subsequent additions to the provider's Outcomes Index 190 are based on these new prognosis ratings. Under this embodiment, the RRFs 180 themselves should exclude all survey score sets involving significant co-morbidities. This embodiment has the advantage that estimates of the RRFs will usually have a smaller variance than if co-morbidities are included in the data set, but the predicted recovery scores 185 are likely to be less accurate than if no co-morbidities were present.

Another embodiment applies a comprehensive econometric model that measures the effects of illness and injury, including co-morbidities, on remaining life-years. It is preferred that the model be estimated with data on patients who have already gone through their life span, including patients who have died from natural causes.

Different applications using QALY measurements often involve adding together changes in QALYs for different individuals. For example, when assessing the efficacy of a drug, the QALYs of patients receiving a placebo may be compared with the QALYs of patients receiving the target drug. However, the legitimacy of adding together or comparing different persons' QALYs likely would be challenged by many economists, because it entails making interpersonal comparisons. The implicit assumption is that a one-QALY change represents the same quality-of-life change for each individual. Although the current invention can make use of the QALY unit, no interpersonal comparisons are made. The output of the current invention is in terms of how each patient regards her recovery, given her original expectations based on her prognosis rating. It gives rise to the following types of statements: Doctor A's patients with a prognosis rating of X and treated for medical condition Y reported an average increase in their quality-of-life of Z % above their expectations; by comparison, Doctor B's patients with a prognosis rating of X' and treated for medical condition Y' reported an average decrease in their quality-of-life of Z'% below expectations.

Consider the relationship $$Y = a_0 + a_1 A + b_1 D_1 + \ldots + b_n D_n + c_1 P_1 + \ldots + c_n P_n + d_{12} D_1 D_2 + d_{13} D_1 D_3 + \ldots + d_{ij} D_i D_j + \ldots + u,$$

where A is the age of the patient; $P_d$ is the prognosis rating for illness d (d=1, ..., n), $P_d = 0$ if the illness is not present; $D_d$ is a dummy variable with a value of 1 if the illness d is present, 0 if it is not present; $D_d D_{d'}$ is a term for the interaction between illness d and illness d'; Y is the time between the patient's original diagnosis and the time of death, which may be measured in quality-adjusted life-years; $a_0, a_1, b_1, \ldots, b_n, c_1, \ldots, c_n, d_{12}, d_{13}, \ldots d_{ij} \ldots$ are parameters to be estimated; and u is a random error term.

The model states that the value of Y depends on the age of the patient, the illnesses that the patient has been diagnosed with, and the patient's prognosis ratings for those illnesses. For some illnesses, the gender and/or ethnicity of the patient are also relevant.

The dummy variables $D_i$ (i=1, ..., n) exclude from the model illness(es) that are not currently present, but they also distinguish between the case where an illness is present and the prognosis rating is 0.0 (D=1; P=0.0) from the case where the d-th illness is not present (D=0; P=0.0).

The interaction term, $D_i D_j$, is designed to measure any effects that are in addition to the individual effects of the two illnesses. In other embodiments, the model can include terms such as $D_i D_j D_k$ to measure the additional effects due to tri-morbidities, etc.

This econometric model provides an estimate of the effect of different types of illness and injury, as well as co-morbidities, on expected remaining life. In another embodiment, the model is extended by adding a time dimension that estimates the effects of varying time intervals between the onsets of each morbidity.

In yet another embodiment, the model is estimated with the Outcomes Index of the treating doctor as an independent variable and expected remaining life as the dependent variable. This model can be used to predict the effect on expected remaining life of treatment by doctors with different Outcomes Indexes.

In Case of Death

When a person dies, quality-adjusted life is assumed to fall to zero. This can have a substantial impact on a doctor's Outcomes Index 190, so it is important to measure this effect as accurately as possible. This raises two related issues: 1) if a patient dies prematurely, how do we penalize the doctor's Outcomes Index if it is unclear to what extent the death is related to the medical condition that the doctor was treating; and 2) how long after the patient's treatment and to what extent should a doctor be penalized for the patient's death?

In one embodiment, a "statute of limitations" can be applied to the patient's recovery score. For example, if a patient dies more than five years after the initial diagnosis, we could assume that the patient's death is due to other causes, and/or we could weight the impact on the recovery score by the likelihood that the disease in question is the primary cause of the patient's death, declining from, say, 100% in the first year to 20% in the fifth year.

In another embodiment, the econometric model described above is estimated. Compute Y for a single patient, using estimated values for the parameters. If the patient dies in less than Y years, then future QALYs are lost, where future QALYs are equal to the area under the predicted RRF between the time of death and the time at which the predicted RRF crosses the death line (abscissa=$RRF_0$ in FIG. 3). In another embodiment, the cause-of-death entry on the patient's death certificate could be used. The problem here is that it is the patient's treating provider who fills out the death certificate, and, as such, he has an incentive to enter a cause of death that has the most favorable impact on his Outcomes Index 190.

Figure 5:
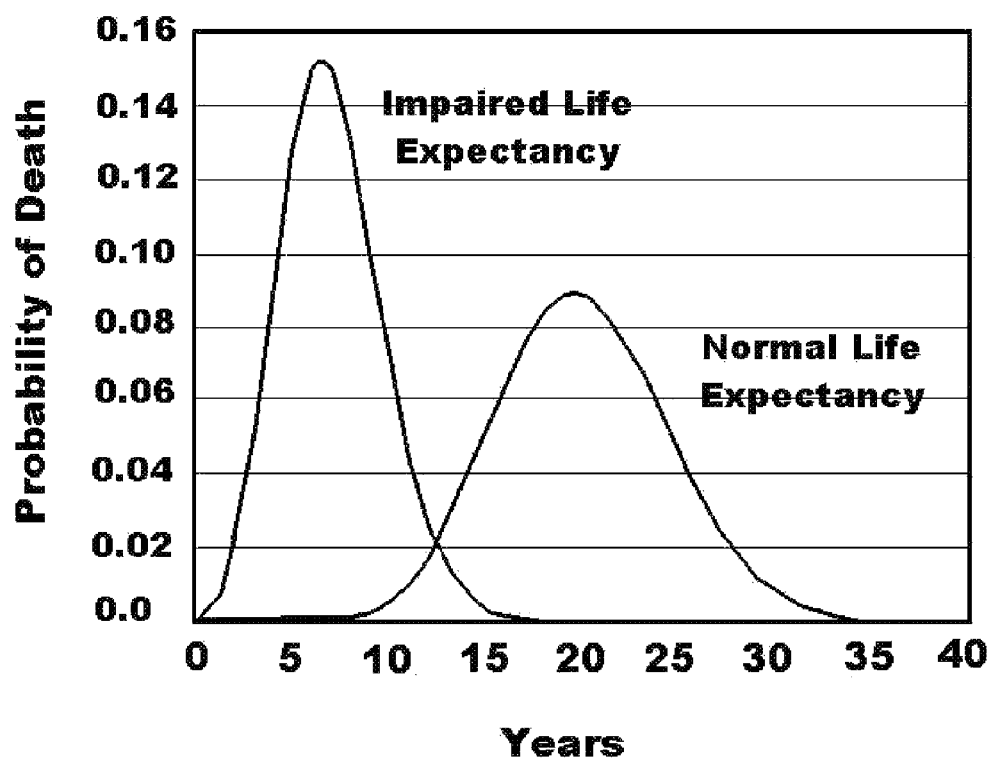
FIG. 5 illustrates probability distributions for the remaining life of a healthy 55-year-old male and an impaired 55-year-old male.

The preferred embodiment uses statistical methods to estimate the probability distributions shown in FIG. 5. The example distribution on the left shows the probability of death as a function of time based on a diagnosis for a 55-year-old male with a specific illness and prognosis rating. The probability of death is equal to the area under the curve between two time periods. The probability distribution on the right shows the probability of death, but for a 55-year-old male with no disease present. Technically, this distribution should represent a person with no disease present, and who does not die from the disease in question.

In this example the two curves cross at about 12 years from the time of the initial diagnosis; thus, if the person dies at twelve years, it is equally likely that death is due to the illness as from some other cause. In this case, half of the loss of future QALYs can be attributed to the illness, where future QALYs are measured as above.

The loss of QALYs due to death at other times can be estimated as follows. Let $y=f(t)$ and $z=g(t)$ be the respective probability distributions for normal and for impaired life expectancy, and $F(t)$ and $G(t)$ be the corresponding cumulative probability distributions. Let $t.sub.d$ be the time of death, where time is measured as the number of years following the initial diagnosis. Then the appropriate weight to apply to the loss of future QALYs is $(1-G(t.sub.d))/(2-F(t.sub.d)-G(t.sub.d))$.

In some applications, it is preferred to discount future QALYs.

In the parent application to this divisional application, it was demonstrated how the process of collecting information, processing the information and producing an outcomes index can be fully automated for a health plan administrator. All required inputs are entered into the system by patients or providers; no additional inputs are required from the health plan administrator. The full automation of this process makes it economically feasible to include as part of a provider's outcomes index every health-plan member's outcome from a non-routine medical episode.

Figure 6:
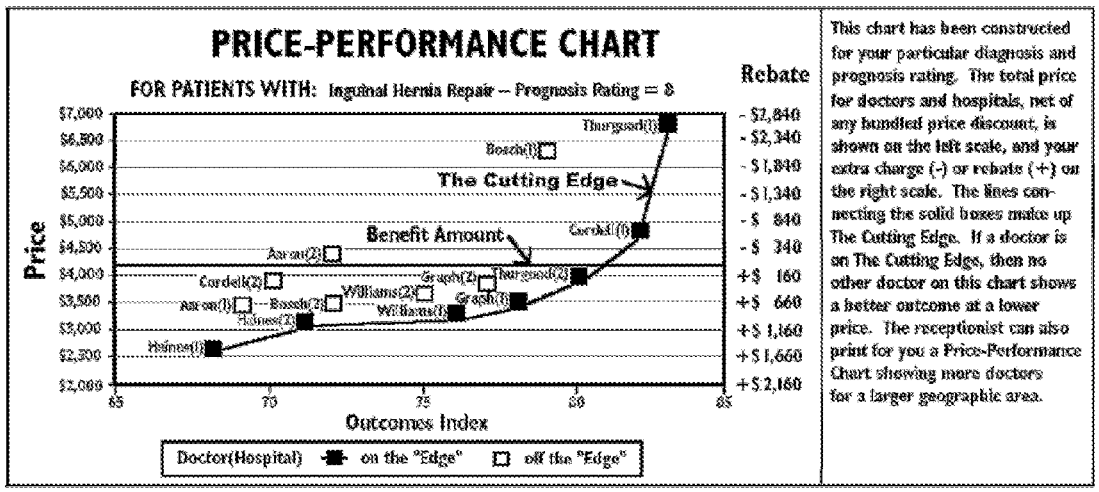
FIG. 6 is an example of a comparative report that incorporates the present invention.

In one embodiment of providing comparative information about treatment providers, FIG. 6 provides an example using an Outcomes Index. The Outcomes Index described herein is used to enable, for instance, a patient to compare for the patient's specific diagnosis and prognosis rating, outcomes indexes for potential treatment providers. The Doctor Shopper.sup.SM report, as shown in FIG. 6 and developed by the inventor as an example of the use of the Outcomes Index, clearly demonstrates how patients and health care providers may beneficially use the Outcomes Index.

Based on self-administered survey data in a database and by automatically processing data in the database, one may generate comparative reports that may include an Outcomes Index.

A comparative report that is provided as an aspect of the present invention may use tables, text, graphs or other textual and graphical means to reflect an Outcomes Index. A comparative report may be used by an insured for selecting a treatment provider and/or hospital. A comparative report may also be used by insurers for ratings of care providers such as physicians and hospitals. A comparative report may also be used by hospitals to rate their own performance and to take measures for performance improvements. A comparative report may be used by an insured for selecting an insurer and its health care network. It may also be used for any other provider that affects the outcome of a treatment of a patient. Accordingly a comparative report that may include an Outcomes Index is a decision support document.

A method here provided as an aspect of the present invention can be performed by a processor that is part of a system. The steps of a method can be stored as instructions in a memory that can be accessed by the processor. A processor may be a distributed processor that may include more than one individual processor and may reside in different physical locations. It may also reside in a single computer device. A processor may act upon data that is retrieved from a database, and it may store results in a database. A database may comprise different storage locations as different individual databases. Databases and processors may be connected to a network. Work stations, such as personal computers, may be used to communicate with a processor and/or a database. Data may be retrieved through the network or provided to a database or a processor through the network. The network may be a private network. It may also be a public network, such as the Internet. On-line in the context of the present invention means communicating with a processor or database, possibly through a workstation or any other computing or communication device including a wireless device, wherein a device is connected to the processor and/or database through a network including the Internet.

The following reference is generally descriptive of the background of the present invention and is hereby incorporated herein by reference: Cost-Effectiveness in Health and Medicine, Gold, Marthe R., Louise B. Russell, Joanna E. Siegel, Milton C. Weinstein. Oxford University Press, New York. 1996.

While there have been shown, described and pointed out fundamental novel features of the invention as applied to preferred embodiments thereof, it will be understood that various omissions and substitutions and changes in the form and details of the device illustrated and in its operation may be made by those skilled in the art without departing from the spirit of the invention. It is the intention, therefore, to be limited only as indicated by the scope of the claims appended hereto.

The invention claimed is:

1. A computerized method for measuring the performance of a medical treatment provider, comprising the steps of:
   a) providing a processor; a memory in communication with said processor; the memory including program code executable by said processor; data entry means; and data for a database;
   b) providing a processing system, comprising:
      i. said database, comprising:
         1. data originating from enrollment of insured patients;
         2. surveys of said insured patients;
         3. medical data, including data relevant to determining prognoses of said insured patients;
         4. data originating from vendors providing: diagnostic codes and their descriptions for each of a plurality of diagnoses; procedure codes and their descriptions for each of a plurality of procedures; and death notices to include the insured population; and 5. historical patient data relating to quality of life, comprising patient outcomes ratings by diagnostic code or type of illness or injury, said outcomes ratings based on a prognosis rating versus an outcomes measure of prior patients;

ii. first processing means for producing for an insured patient a treatment plan that specifies the identity of said insured patient, at least one procedure to be provided, and a prognosis rating;

iii. second processing means for producing a treatment record that specifies at least one procedure actually provided to said insured patient;

iv. third processing means for calculating at least one recovery score for said insured patient and modifying said outcomes index of said medical treatment provider to include said recovery score of said insured patient; and c) accessing said database to add said insured patient's said prognosis rating, said recovery score and said death notice, if any; and said medical treatment provider's said modified outcomes index, whereby the improvement comprises the ability to compare the outcomes index of one medical treatment provider with the outcomes index of other medical treatment providers with respect to a given diagnosis and for patients with comparable prognosis ratings;

d) producing a set of reference recovery functions (RRFs) for each of a plurality of types of illnesses or injuries from historical patient data relating to quality of life;

e) generating a predicted recovery score for a patient of said medical treatment provider by combining said set of RRFs and the prognosis rating of said patient for an episode of illness or injury, and where said prognosis rating is produced independently of said medical treatment provider, whereby said independently produced prognosis rating can provide an unbiased prognosis rating;

f) administering a survey of the signs and symptoms of said patient, wherein: each said sign or symptom is caused by said episode of illness or injury; each said sign or symptom is assigned a severity score corresponding to said patient's perception of the severity of said sign or symptom; and each said sign or symptom is assigned a weight corresponding to the relative intensity with which said patient desires to eliminate said sign or symptom;

g) calculating a survey score, comprising the normalized sum of the products of said severity scores and their corresponding said weights, whereby said survey score is a measure of quality-of-life status;

h) generating a personal recovery function by combining with said set of RRFs a plurality of said patient's survey scores obtained at different times, wherein said plurality of said patient's survey scores constitutes a survey score set;

i) calculating an actual recovery score from said personal recovery function; and j) calculating an outcomes measure by combining said predicted recovery score with said actual recovery score.

2. The method as claimed in claim 1, combining the outcomes measures of a plurality of medical treatment provider's past patients, said patients falling within a given prognosis rating group and with the same type of illness or injury, to produce an outcomes index, whereby each said outcomes index is a measure of the performance of said medical treatment provider with respect to said prognosis rating group and said type of illness or injury.

3. The method as claimed in claim 2, providing a comparative report wherein the outcomes indices with respect to the same prognosis-rating group for a given type of illness or injury are compared for a plurality of treatment providers.

4. The method as claimed in claim 3, further including a comparative report that includes a value chart depicting each said medical treatment provider's outcomes index and treatment cost, whereby the value of treatments administered by said medical treatment providers can be compared.

5. The method as claimed in claim 1, providing the self-administering of said survey by said patient.

6. The method as claimed in claim 1, providing that said RRFs and said severity scores are expressed in units compatible with quality-adjusted life-years.

7. The method as claimed in claim 1, providing generating a set of RRFs for a given type of illness or injury, comprising the steps of rank ordering said survey scores, dividing said survey scores into n groups and statistically fitting at least one mathematical function through said survey scores within each of said n groups, whereby said statistically fitted functions for each said group comprise an RRF; each RRF is labeled $RRF_1$ through $RRF_n$; $RRF_0$ is a horizontal line below $RRF_1$ that corresponds to the state of death; and $RRF_{n+1}$ is a horizontal line above $RRF_n$ that corresponds to the bliss state.

8. The method as claimed in claim 7, providing said steps of rank ordering said survey scores is selected from the methods consisting of rank ordering according to the arithmetic means of said survey score sets and rank ordering by said prognosis ratings associated with said survey score sets, wherein the method of rank ordering according to the means of said survey score sets comprises the following steps:

a) computing the arithmetic mean of each of a plurality of survey score sets associated with a given type of illness or injury;

b) ranking said arithmetic means in ascending order; and c) dividing said rank ordered arithmetic means into said n groups, where each n corresponds to a prognosis rating group, and n is greater than 2; and wherein the method of rank ordering by prognosis ratings comprises the following steps:

a) ranking in descending order said survey score sets with respect to their corresponding prognosis ratings; and b) dividing said rank-ordered prognosis ratings and their corresponding survey score sets into said n groups, whereby patients facing similar treatment and recovery risks are grouped together as a means for controlling for risk.

9. The method as claimed in claim 7, calculating a predicted recovery score, PS, for said patient whose prognosis rating is x, according to the steps: calculating the two areas $A_{k'+1}$ and $A_{k'}$, under the two RRF curves $RRF_{k'+1}$ and $RRF_{k'}$, where $k'+1$ is the number of the RRF immediately greater than x and $k'$ is the number of the RRF immediately smaller than or equal to x; and calculating said predicted recovery score as:

$$PS = (A_{k'} + [x - \text{int}(x)](A_{k'+1} - A_{k'}))/S,$$

where S is the highest possible survey score.

10. The method as claimed in claim 7, providing that said patient's survey score sets for a given episode of illness or injury are further subdivided into a plurality of recovery phases, and a mathematical function is statistically fitted through the survey scores within each said recovery phase, whereby said RRF is comprised of a plurality of fitted functions, each said fitted function corresponding to a recovery phase.

11. The method as claimed in claim 7, generating said personal recovery function for said patient, comprising the steps:
   a) for each pair of consecutive survey scores taken over time, dividing the line segment connecting said survey scores into sub-segments, as necessary, such that each sub-segment lies wholly between two successive RRFs; and
   b) interpolating the path of said personal recovery function between said survey scores such that said personal recovery function passes through both survey scores, the curvature of said personal recovery function is based on the curvatures of the RRFs immediately above and immediately below said line segment, and the curvature characteristics of said personal recovery function are a weighted average of the curvature characteristics of said RRFs, where the weights are inversely proportional to the vertical distances of said line segment from said RRFs.

12. The method as claimed in claim 11, calculating an actual recovery score from said personal recovery function comprising the following steps: computing the area under each said sub-segment, totaling the areas under all said sub-segments and dividing said total area by the highest possible survey score over the time period encompassing said surveys.

13. The method as claimed in claim 1, updating said outcomes index of a provider to include outcomes measures of more recent patients of said provider and, optionally, dropping outcomes measures of less recent patients with the same type of illness or injury, whereby said outcomes index reflects outcomes based on the latest techniques and technologies used in treating said type of illness or injury.

14. The method as claimed in claim 1, providing the administrator of a health plan with a fully automated process for generating outcomes indices of medical treatment providers who treat members of said health plan, whereby all of the data inputs required to produce outcomes indices are provided in digital form by patients, providers and at least one vendor providing death notices.

15. The method as claimed in claim 1, calculating an outcomes measure as $$M_{dp}^* = (\Sigma_i (RS_{idp}/years_i))/I,$$

where RS is the actual recovery score, $years_i$ is the total number of actual years spanned by the recovery scores of the i-th patient, and I is the total number of patients.

16. The method as claimed in claim 1, calculating an outcomes measure as $$M_{dp}^+ = (\Sigma_i (RS_{idp}/PS_{idp}))/I,$$

where RS is the actual recovery score, PS is the predicted recovery score and is the total number of patients.

17. The method as claimed in claim 1, calculating an outcomes measure as $$M_{dp}^\# = \Sigma_i RS_{idp}/\Sigma_i PS_{idp},$$

where RS is the actual recovery score and PS is the predicted recovery score.

18. The method as claimed in claim 1, statistically estimating an outcomes measure as $$Y_{idp} = b_0 + b_1 M_{idp}^* + b_2 M_{idp}^\# + b_3 PR_{idp} + b_4 \ln Q_{idp} + u,$$

where $M_{dp}^* = (\Sigma_i (RS_{idp}/years_i))/I$; $M_{dp}^\# = \Sigma_i RS_{idp}/\Sigma_i PS_{idp}$;

and where PR is the prognosis rating; ln Q is the natural logarithm of the number of times the provider has treated said type of illness or injury; RS is the recovery score, PS is the predicted score, $years_i$ is the total number of actual years over which the recovery score is measured, I is the total number of patients being scored, and u is a random error term.

19. The method as claimed in claim 1, statistically estimating for patients with co-morbidities the relationship:

$$Y = a_0 + a_1 A + b_1 D_1 + \ldots + b_n D_n + c_1 P_1 + \ldots + c_n P_n + d_{12} D_1 D_2 + d_{13} D_1 D_3 + \ldots + d_{ij} D_i D_j + \ldots + u,$$

where A is the age of said patient, $D_i$ (i=1, ..., n) is a dummy variable with a value of 1 if the illness i is present, 0 if it is not present, $D_i D_j$ is a term for the interaction between illness i and illness j, $P_i$ is the prognosis rating for illness i, where $P_i = 0$ if illness i is not present, Y is the time between the patient's original diagnosis and the time of death, $a_0, a_1, b_1, \ldots, b_n, c_1, \ldots, c_n, d_{12}, d_{13} \ldots d_{ij} \ldots$ are parameters to be estimated, and u is a random error term.

20. The method as claimed in claim 1, determining any expected loss of life attributable to a diagnosed illness or injury and its treatment, comprising, for a patient with given risk factors prior to said diagnosed illness or injury, comparing the pre-diagnosis probability distribution of the life expectancy of a population with said risk factors with the probability distribution of the life expectancy for a preferably deceased population with said patient's same risk factors, but with no history of said diagnosed illness or injury, whereby any expected loss of life attributable to said diagnosed illness or injury within a given time period can be determined by a person skilled in the art.

* * * * *